US00PP27190P3

(12) United States Plant Patent
Bagdasarian

(10) Patent No.: US PP27,190 P3
(45) Date of Patent: Sep. 27, 2016

(54) STRAWBERRY PLANT NAMED 'RUBY JUNE'

(50) Latin Name: *Fragaria×ananassa*
Varietal Denomination: Ruby June

(71) Applicant: Jimmy Haig Bagdasarian, Santa Cruz, CA (US)

(72) Inventor: Jimmy Haig Bagdasarian, Santa Cruz, CA (US)

(73) Assignees: Jimmy H. Bagdasarian, Santa Cruz, CA (US); Lassen Canyon Nursery, Inc., Redding, CA (US)

( * ) Notice: Subject to any disclaimer, the term of this patent is extended or adjusted under 35 U.S.C. 154(b) by 72 days.

(21) Appl. No.: 14/544,375

(22) Filed: Dec. 29, 2014

(65) Prior Publication Data

US 2016/0192555 P1 Jun. 30, 2016

(51) Int. Cl.
*A01H 5/08* (2006.01)

(52) U.S. Cl.
USPC ..... Plt./209

(58) Field of Classification Search
USPC ..... Plt./209
See application file for complete search history.

*Primary Examiner* — Annette Para
(74) *Attorney, Agent, or Firm* — Catherine Ashley Straight

(57) ABSTRACT

A new and distinct variety of strawberry plant named 'Ruby June.' This new short day strawberry variety which is partially remontant, exhibiting everbearing tendencies. The variety is characterized by plants with medium to high vigor which produce large, firm conical fruit with great flavor, and an attractive medium red exterior color and a warm red interior color.

6 Drawing Sheets

Latin name of the genus and species of the plant claimed: *Fragaria×ananassa.*

Variety denomination: 'Ruby June'.

BACKGROUND OF THE INVENTION

1. Field of Invention

The present invention relates to a new and distinct variety of strawberry named 'Ruby June.' This new short day strawberry variety is the result of a controlled cross in an ongoing breeding program made by the inventor, Jimmy Bagdasarian, in 2008. The variety is botanically known as *Fragaria×ananassa.*

The primary market for the 'Ruby June' variety is for the fresh market sales of the fruit. 'Ruby June' produces large conical berries with few creases, and with good firmness.

2. Description of Relevant Prior Art

The controlled cross, conducted in the ongoing breeding program, which resulted in the 'Ruby June' variety, was between the strawberry variety designated '10B131,' a male, and a strawberry variety designated '2G16,' a female.

The male parent, '10B131,' is an unreleased proprietary variety having the following characteristics: medium day-neutral; globose habit; tight density; leaves which are dark green in color; and, the variety exhibits medium plant vigor.

The female parent, '2G16,' is an unreleased proprietary variety having the following plant characteristics: strong short day; compact growth habit; leaves have low glossiness with considerable blistering, and are dark green in color; medium firm fruit has an excellent flavor, and an attractive medium red interior color; and the variety exhibits medium plant vigor.

The leaves of 'Ruby June' have medium glossiness and exhibit medium leaf blistering in comparison to the leaves of the female parent, '2G16,' which have low leaf gloss and considerable leaf blistering. The leaf color of 'Ruby June' is dark green like both of its parent varieties.

The aforementioned controlled cross was carried out in a breeding program at Santa Cruz, Calif., USA. Pollen taken from a male '10B131' plant pollinated a '2G16' female plant. The flowers were covered so that no other pollen could contaminate the procedure.

Strawberries developed, were later harvested and the seeds resulting from this cross were extracted and germinated in a greenhouse at Redding, Calif., USA. The resulting seedlings were transplanted to Shastina, Calif. in 2009, grown for an additional period of time and allowed to propagate asexually. Plants were then harvested and planted in breeding plots in early to mid-October in: Oxnard, Calif. (Ventura County); and Watsonville, Calif. (Monterey County). The selection of the new variety was first made in Watsonville, Calif. This selection was designated '33K46' in 2010.

The new variety underwent further testing and was propagated asexually by stolons in breeding plots. Further testing was conducted under growing conditions present in both Northern and Southern districts in test plots in: Macdoel, Calif. (Siskiyou County); and Manteca, Calif. (San Joaquin County).

The new variety has also been "meristemed." Small pieces of plant material (approximately 0.5 mm in diameter), consisting of the undifferentiated meristem tissue and one or two leaf primordia, were removed from the buds on crowns of young daughter plants, then placed on nutrient medium, and new plants were grown from them. Planting stock from the "meristemed" plants are growing in a screenhouse located in Redding, Calif.

The new variety was named 'Ruby June.' The propagules of 'Ruby June' ('33K46') are identical to the original plant in all distinguishing characteristics; accordingly, the propagation discussed above has demonstrated that the traits disclosed herein remain fixed and true to type through successive generations of asexual reproduction.

SUMMARY OF THE INVENTION

Ruby June is a short day variety exhibiting the following combination of characteristics, which have been observed repeatedly, and which distinguish this strawberry plant as a new and distinct variety:

1. The variety produces medium to large sized fruit;
2. The fruit is conic, with some periodic tips and creases;
3. The fruit has a medium red exterior color and a medium-light red interior color;
4. The fruit is sweet tasting, with very good flavor;
5. The fruit is firm with good retention of quality, appearance, and firmness;
6. The plants of the variety are characterized by medium high vigor, with a large root system, and a semi-upright growth pattern; and,
7. The variety is partially remontant.

The fruit produced by the 'Ruby June' plant variety is an attractive medium red exterior color with medium high glossiness. The color of the fruit is even all the way to the top.

The fruit of 'Ruby June' demonstrates other characteristics and qualities that are desired by fresh market strawberry sales companies. The medium red color is preferred by many shippers of fresh strawberries over the deeper red colored berries which are more likely to be viewed as overripe by buyers than the lighter colored berries.

The plant vigor of 'Ruby June' is medium when dug early and planted immediately; however, plant vigor is high in Northern districts when plants are dug late. Runner production also varies with the location of the planting, with lower runner production in Southern districts and moderate runner production in Northern districts.

BRIEF DESCRIPTION OF THE DRAWING

The accompanying color photographs, identified as FIGS. 1 through 7, show the appearance of typical specimens of the new strawberry variety, initially designated '33K46,' and now named 'Ruby June.'

These Figures depict the colors, as nearly true as it is reasonably possible given differences in color illustrations of this character. Accordingly, color in the photographs may differ slightly from the colors discussed in the botanical description.

DETAILED BOTANICAL DESCRIPTION OF THE PLANT

Figure 1:
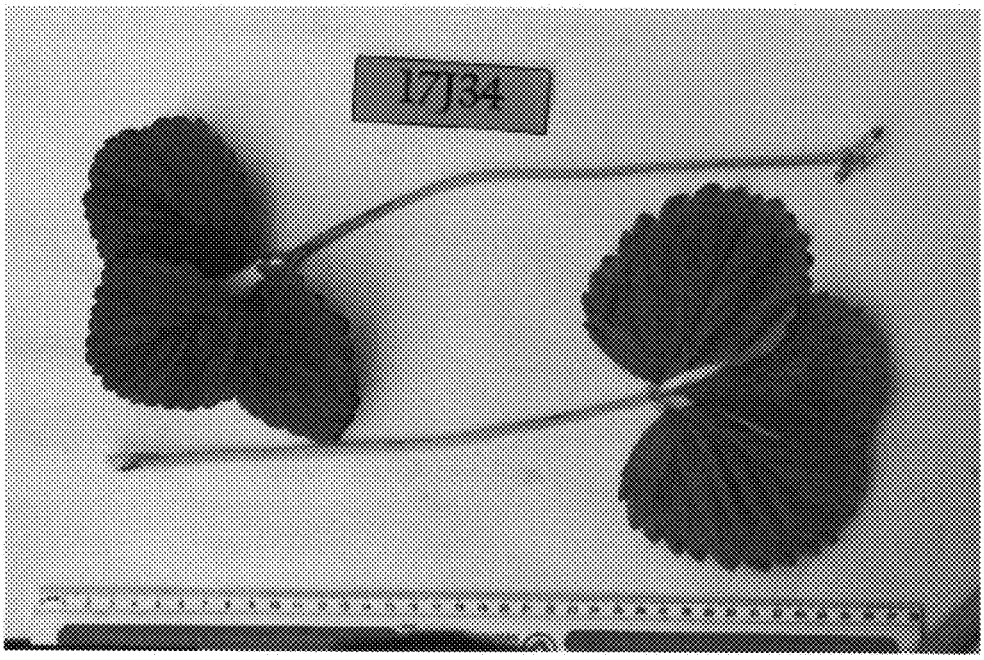
FIG. 1 shows typical leaf and petiole structures of 'Ruby June' at mid-season.
Figure 2:
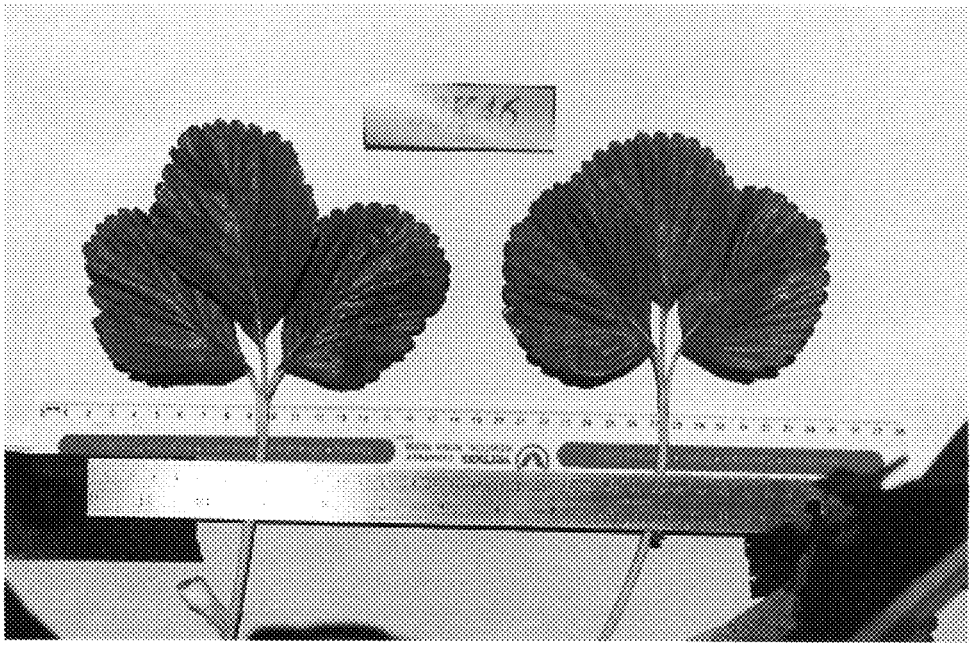
FIG. 2 shows typical leaf structure.
Figure 3:
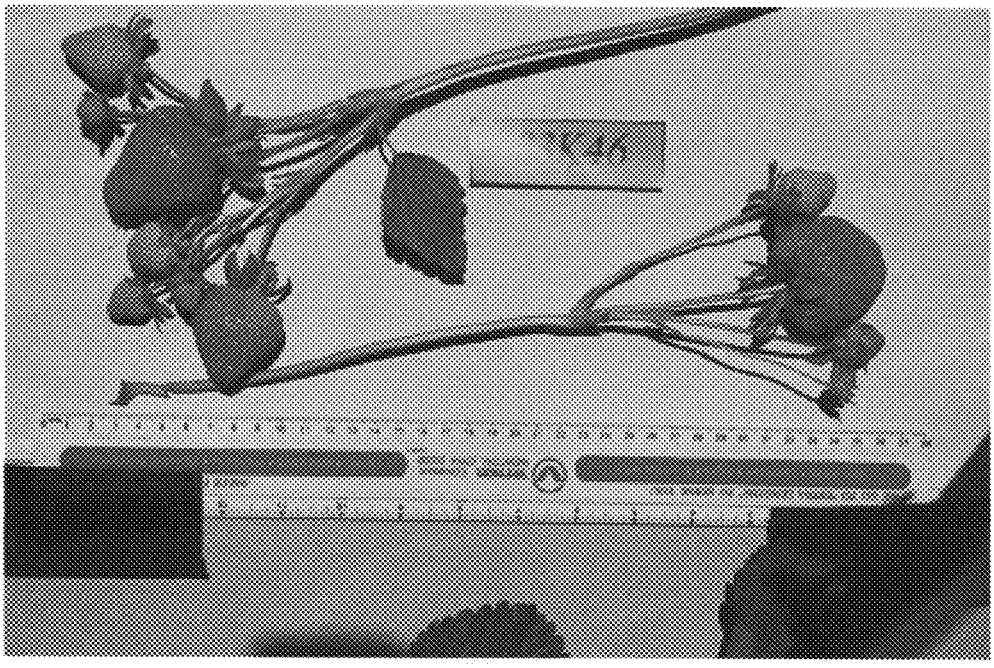
FIG. 3 shows a selection of typical mid-season fruit.
Figure 4:
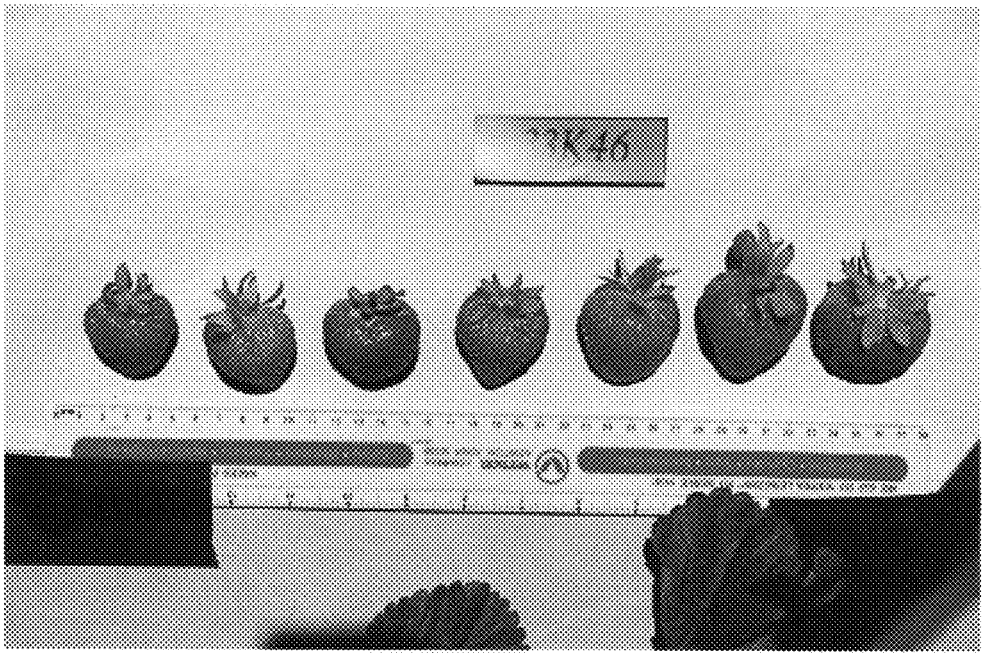
FIG. 4 shows typical fruit shape and calyx position over the berry of 'Ruby June'.
Figure 5:
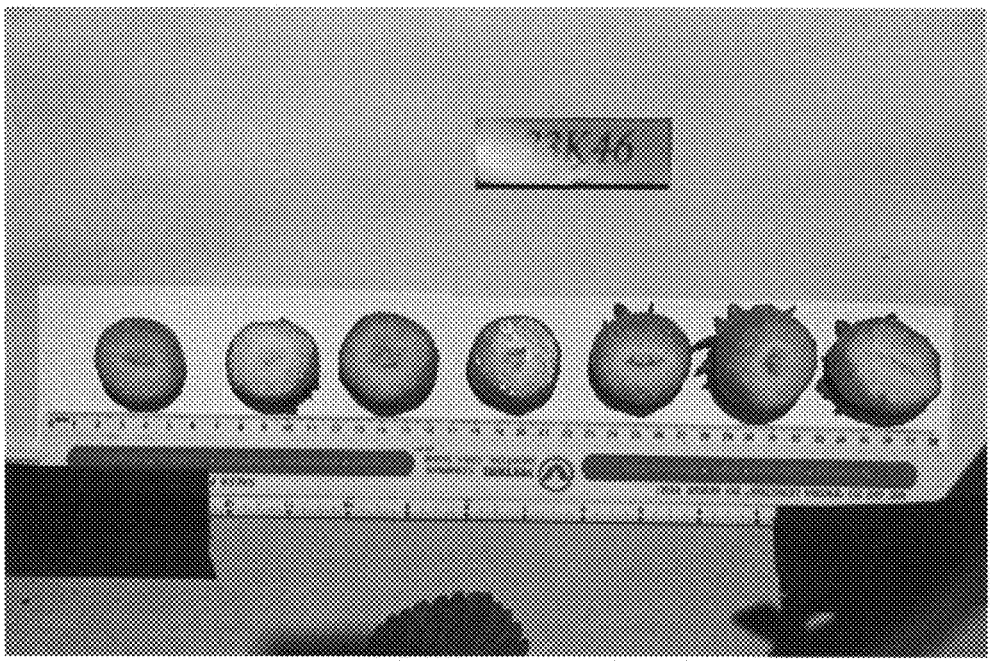
FIG. 5 shows a transverse cross-section of typical fruit internal coloration and core size; and, FIG. 6 shows typical fruiting plants in a field.
Figure 6:
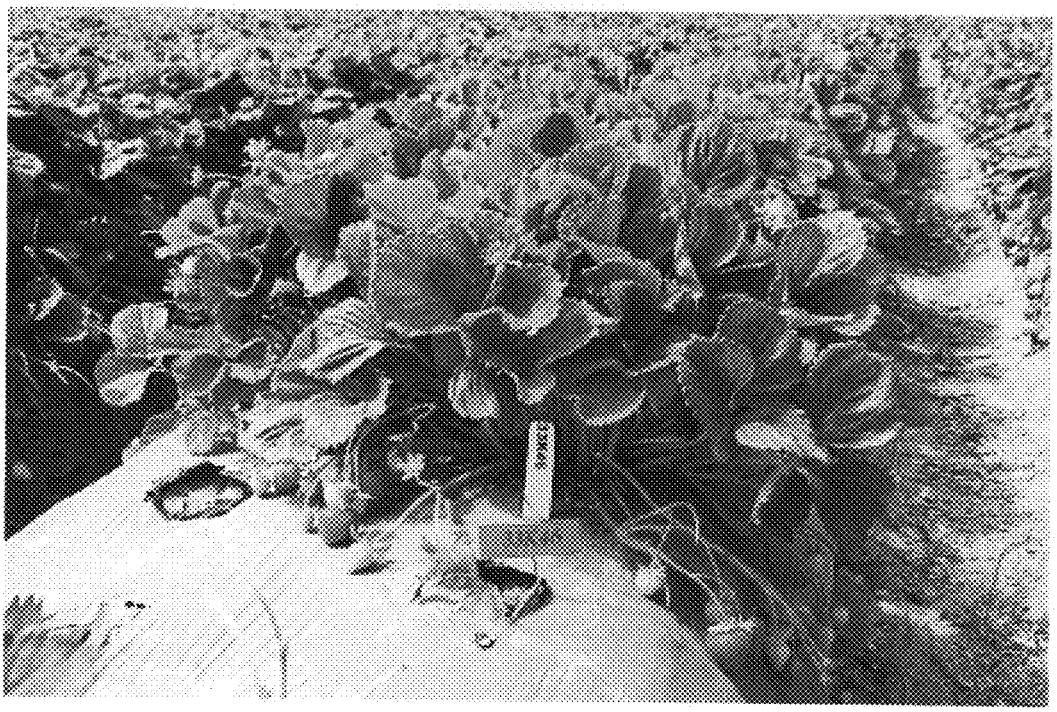

'Ruby June' is a new and distinct variety of strawberry, genus and species *Fragaria×ananassa*. It is the result of a cross between its male parent, '10B131,' an unreleased proprietary variety, and '2G16,' its female parent. The male parent, '10B131,' is a medium day neutral variety, and female parent, '2G16,' is a strong short day variety. 'Ruby June' is a short-day variety with everbearing tendencies. The plants of the new variety have a semi-upright growth habit, with medium high vigor and a large root system. 'Ruby June' exhibits several characteristics which are improvements over one or both of its parent varieties, and/or other known cultivars. The characteristics of 'Ruby June' were observed in plants aged four to eight months from planting. These characteristics and comparisons with other cultivars are discussed following.

The various data set forth for 'Ruby June' in Tables 1, 2, and 3 was collected and evaluated in 2012 through 2014, from plants grown at the Meridian ranch test plot, in Prunedale, Monterey County, Calif. Color terminology where noted herein for 'Ruby June' is in accordance with the Panton Color Formula Guide GP 1201.

In Table 1, the observed characteristics of 'Ruby June' are set forth.

TABLE 1

Detailed Description of Characteristics of 'Ruby June'

| | |
|---|---|
| SPECIFICATION: | |
| Genus/Species | *Fragaria × Ananassa.* |
| Market name | Strawberry. |
| PARENTS: | |
| Male | Proprietary variety '10B131' (unpatented). |
| Female | Proprietary variety '2G16' (unpatented). |
| PLANT: | |
| Type | Short Day with everbearing tendencies. |
| Growth habit | Upright. |
| Foliage density | Dense. |
| Vigor | Medium to high. |
| Height | Average: 33.8 cm; range: 31 cm to 37 cm. |
| Width | Average: 46.9 cm; range: 38 cm to 56 cm. |
| Crowns | Multiple crowns produced early after planting. |
| Disease tolerance | Test plants, grown in plots in areas with disease pressure, have shown excellent tolerance. In early observations of plants grown in a coastal California area, plants have exhibited excellent tolerance to *Fusarium oxysporum* (Fusarium wilt) as compared to 'Monterey' cultivar plants grown in the same area. |
| LEAF: | |
| Width | Average: 21.95 cm; range: 19.5 cm to 24.5 cm. |
| Color | Adaxial Surface: green 350 U.<br>Abaxial Surface: green 364 U. |
| Pubescence | Medium density. |
| Inter-vein blistering | Medium. |
| Glossiness | Medium. |
| Variegation | None. |
| TERMINAL LEAFLET: | |
| Length | Average: 11.31 cm; range: 9.0 cm to 13.3 cm. |
| Width | Average: 8.42 cm; range: 6.6 cm to 9.6 cm. |
| Ratio length to width | 1.34. |
| Margin | Serrate to crenate. |
| Leaf shape | Orbicular. |
| Base shape | Acute. |
| Cross-section shape | Concave. |
| PETIOLE: | |
| Pubescence | Medium-high density; direction: almost perpendicular. |
| Petiole color | Green 365 U. |
| Petiole length | Average: 21.75 cm; range: 17.5 cm to 25 cm. |
| Petiole diameter | Average: 4.93 mm; range: 3.9 mm to 5.8 mm. |

TABLE 1-continued

| Detailed Description of Characteristics of 'Ruby June' | |
|---|---|
| STIPULE: | |
| Stipule anthocyanin coloration | Present, but mild. |
| Length | Average: 33.15 mm; range 28.1 to 38.0 mm. |
| Width | Average: 15.4 mm range 10.9 to 22.9 mm. |
| STOLON: | |
| Stolon anthocyanin coloration | Present; medium intensity. |
| Pubescence | Medium high; upward direction. |
| Diameter | Average: 4.0 mm; range: 3.5 mm to 4.4 mm. |
| INFLORESCENCE: | |
| Flowering time | Early. |
| Position | Primary bract at or below foliage with bloom above foliage |
| Number of blooms | Average: 4.7; range: 3 to 8. |
| Length | Fruiting clusters mid-season: average 32.45 cm; range: 25 cm to 39.5 cm. |
| Flower | Average diameter: 27.31 mm; range: 19.37 mm to 34.12 mm. |
| Petal arrangement | Touching. |
| Petals | Average number per flower: 5.2; range: 5 to 6. |
| Petal Length | Average: 11.8 mm; range: 9.1 mm to 13.7 mm. |
| Petal Width | Average: 10.75 mm; range: 8.1 mm to 13.4 mm. |
| Ratio length to width | 1.10. |
| Petal Color | Upper side: white, 11-4201 TPX. |
| Calyx | Size in relation to corolla: slightly larger. |
| Calyx color | Adaxial Surface: green 364 U. Abaxial Surface: green 370 U. |
| Stamens | Average number: 23.5; range 21 to 34. |
| Pedicel | Attitude of hairs is upwards oblique. |
| FRUIT: | |
| Bearing | Partially remontant. |
| Shape | Conical. |
| Length | Average: 4.4 cm; range: 3.6 cm to 5.0 cm. |
| Width | Average: 3.6 cm; range: 3.3 cm to 4.0 cm. |
| Ratio length to width | 1.22. |
| Size | Average grams per berry: 30.48 g. |
| Achenes | Sunken below, to slightly protruding from, the fruit surface. |
| Glossiness | Medium high. |
| External color | Medium red 1797 C |
| Internal color | Flesh, excluding core: Pantone Warm Red C |
| Evenness of external color | To the top of berry. |
| Width of band at top devoid of achenes | Small. |
| Fruit center | Little to some hollowness. |
| Firmness | Moderately firm, but less than the very firm fruit of 'Sweet Ann.' |

In Table 2, the foliar characteristics of 'Ruby June' are compared with the varieties 'Aromas' (U.S. Plant Pat. No. 10,451), 'Sweet Ann' (U.S. Plant Pat. No. 22,472) and 'Albion' (U.S. Plant Pat. No. 16,228). In Table 3, the flower and fruit characteristics of 'Ruby June' are compared with the varieties 'Sweet Ann' (U.S. Plant Pat. No. 22,472) and 'Albion' (U.S. Plant Pat. No. 16,228). In Table 4, comparison of leaf and fruit colors is made between 'Ruby June' and several commercially grown cultivars.

Color terminology where noted herein respecting all cultivars, except 'Albion,' is in accordance with the Pantone Color Formula Guide. Color terminology respecting 'Albion' is in reference to the Munsell color system.

Plants and Foliage

The form and structure of the plants of 'Ruby June' are semi-upright with dense foliage. In comparison, the plants of 'Sweet Ann,' which has the same male parent ('10B131') as 'Ruby June', are erect and open. The plants 'Ruby June' are slightly shorter than those of 'Sweet Ann.' However, the plant spread or width of 'Ruby June' is significantly greater than any of the comparison varieties. The plants of 'Ruby June,' are large in comparison to many other commercial cultivars grown in fresh strawberry production fields in California. 'Ruby June' also exhibits high plant vigor in the Northern districts.

In Table 3, comparative data for plant and leaf characteristics for 'Ruby June,' 'Aromas,' 'Sweet Ann' and 'Albion' are set forth.

TABLE 2

Foliar Characteristics of 'Ruby June' Compared to 'Aromas,' 'Sweet Ann,' and 'Albion'

| Foliar | Cultivar Name | | | |
|---|---|---|---|---|
| Characteristic | 'Ruby June' | 'Aromas' | 'Sweet Ann' | 'Albion' |
| Plant height (mm) | | | | |
| Average | 338 | 272 | 380 | 252 |
| Range | 310-370 | 240-300 | 290-480 | 210-270 |
| Plant spread (mm) | | | | |
| Average | 469 | 323 | 420 | 341 |
| Range | 380-560 | 300-360 | 330-510 | 304-394 |
| Leaf width (mm) | | | | |
| Average | 219.5 | 135 | 165 | 135 |
| Range | 195-245 | 120-150 | 130-195 | 105-170 |
| Mid-tier leaflet length (mm) | | | | |
| Average | 113 | 79 | 88 | 73 |
| Range | 90-133 | 70-90 | 72-105 | 50-95 |
| Mid-tier leaflet width (mm) | | | | |
| Average | 84 | 74 | 67 | 68 |
| Range | 66-96 | 60-80 | 52-88 | 50-95 |
| Petiole length (mm) | | | | |
| Average | 217.5 | 174 | 220 | 105 |
| Range | 175-250 | 140-210 | 150-280 | 70-130 |
| Petiole diameter (mm) | | | | |
| Average | 4.93 | 4.5 | 3.74 | 4.1 |
| Range | 3.90-5.80 | 4-6 | 3.01-4.29 | 3.7-4.6 |
| Number leaflets per leaf | 3 | 3 | 3 | 3 |
| Leaf convexity | Concave | Mostly flat to convex | Slight concave | Some flat, most slight concave |
| Shape leaflet base | Acute | Moderately oblique | Obtuse | Obtuse |
| Leaf pubescence | Medium | Moderate density | Medium density | Light-moderate |
| Petiole pubescence | Medium high | Moderate-heavy | Medium density | Heavy density |
| Petiole direction | Nearly perpendicular | Perpendicular | Perpendicular | Perpendicular |
| Stipule length (mm) | | | | |
| Average | 33.15 | 34.2 | N/A | 23.3 |
| Range | 28.1-38.0 | 30-39 | | 14-34 |
| Stipule anthocyanin coloration | Weak yes | Very weak | Weak yes | Yes |

TABLE 2-continued

Foliar Characteristics of 'Ruby June' Compared to 'Aromas,' 'Sweet Ann,' and 'Albion'

| Foliar Characteristic | Cultivar Name 'Ruby June' | 'Aromas' | 'Sweet Ann' | 'Albion' |
|---|---|---|---|---|
| Leaf margins | Serrate to crenate | Rounded to semi-pointed | Commonly crenate | Semi-pointed |
| Leaf color adaxial surface | 350 U | 5GY 4/3 | 364 U | 5GY 5/6 |
| Leaf color abaxial surface | 364 U | 10Y 4/3 | 370 U | 5GY 4/4 |
| Petiole color | 380 U | 5GY 8/8 | 383 U | 5GY 7/10 |
| Leaf surface blistering | Medium | Medium to strong | Very weak | Medium |
| Leaf surface glossiness | Medium | — | Medium | Low |

Flowering and Fruit

'Ruby June' is a short-day variety that is partially remontant. The primary flowers of 'Ruby June' are smaller than those of 'Sweet Ann' and those of 'Albion.' The flowers of 'Ruby June' exhibit five to six petals per bloom, similar to 'Sweet Ann,' and with less variation than the flowers of 'Albion' which range from five to eight petals per bloom.

The fruit of 'Ruby June' has excellent culinary qualities, including: desirable shape and size, lighter red color than 'Albion,' and a sweet strawberry flavor.

In Table 3, comparative data for flower and fruit characteristics for 'Ruby June,' 'Sweet Ann' and 'Albion' are set forth.

TABLE 3

Flower and Fruit Characteristics of 'Ruby June' Compared to 'Sweet Ann' and 'Albion'

| Characteristic | Cultivar 'Ruby June' | 'Sweet Ann' | 'Albion' |
|---|---|---|---|
| Petal number | 5-6 | 5-6 | 5-8 |
| Petal length (mm): Average | 11.8 | 11.21 | 12.7 |
| Petal length (mm): Range | 9.1-13.7 | 9.2-13.13 | 11-15 |
| Petal width (mm): Average | 10.75 | 11.05 | 12.6 |
| Petal width (mm): Range | 8.1-13.4 | 9.0-13.1 | 11-14.0 |
| Position of flower (relative to foliage) | most even, some exposed | most exposed, some even | most exposed, some even |
| Fruit shape | conical | long conical | long conical |
| Fruit length (mm): Average | 44 | 49.4 | 60.5 |
| Fruit length (mm): Range | 36-50 | — | 55-75 |
| Fruit width (mm): Average | 36.3 | — | 49.7 |
| Fruit width (mm): Range | 33-40 | — | 45-55 |

The leaf and fruit colors of 'Ruby June' is readily distinguished from that of several other commercially grown strawberry varieties. The exterior color of the fruit of 'Ruby June' is medium red, which is slightly darker than the medium red color of the 'Sweet Ann' fruit, but lighter than the deeper colored 'Albion' fruit. The interior color of the fruit of 'Ruby June' is lighter than that of 'Sweet Ann' and of 'Albion' fruit.

Table 4 shows the visually observed characteristics of the leaf and fruit colors of 'Ruby June' as compared to the leaf and fruit color characteristics of 'Sweet Ann,' 'Chandler,' 'Camarosa,' 'Albion,' and 'Catalina.'

TABLE 4

Comparison of Leaf and Fruit Colors of 'Ruby June' to Other Cultivars

| Cultivar | Color Adaxial Leaf | Color Abaxial Leaf | Color External Fruit | Color Internal Fruit |
|---|---|---|---|---|
| 'Ruby June' | 364 C | 364 U | 1797 C | Pantone Warm Red C |
| 'Sweet Ann' | 364 U | 370 U | 185 C | 1788 C |
| 'Chandler' | 343 C | 339 U | 186 C | 179 C |
| 'Camarosa' | 349 C | 348 U | 193 C | 185 C |
| 'Albion' | 5GY 3/2 | 5GY 5/6 | SR 3/7 | 7.5R 3/6 |
| 'Catalina' | 343 C | 349 U | 193 C | 185 C |

Leaf samples from 'Ruby June,' along with two advanced proprietary (unpatented) selections from the breeding program: '42J4' and '17J34,' were submitted to a lab for allelic fingerprint comparison to the control variety, "Camarosa," and the over two hundred other varieties of strawberry in its data base. The allelic fingerprint analysis establishes that 'Ruby June' is distinct and unique compared to the lab's large database of allelic fingerprints. Table 5 below sets forth the test results.

TABLE 5

Allelic Fingerprint Analysis

| Cultivar | Ml | M2 | M3 |
|---|---|---|---|
| 'Ruby June' | 206, 224, 229 | 188,190, 216, 232 | 235, 241, 245, 265 |
| '42J4' | 202, 204, 206, 229 | 188, 216, 232 | 235, 241, 245, 269 |
| '17J34' | 204, 206, 214, 229 | 173, 190, 232 | 231, 243, 245, 265, 269 |
| 'Camarosa' | 214, 222, 224, 229 | 188, 190, 216, 232 | 247, 265 |

Performance

Performance with respect to fruit size, yield, and appearance for 'Ruby June' was assessed by making comparisons with 'Sweet Ann,' and two advanced proprietary (unpatented) selections from the breeding program: '42J4' and 33K46.' All plants for these trials were initially grown at a high elevation nursery in Macdoel, Siskiyou County, Calif. The plants of 'Ruby June' and the comparison varieties were then planted and evaluated at the Meridian ranch test plot in Monterey County, Calif. in 2012 and 2013.

The average fruit size of 30.48 grams per berry for 'Ruby June' is smaller than the very large fruit produced by 'Sweet Ann,' the other comparison cultivars, or of 'Albion' (33.0 g/berry). The fruit of 'Ruby June,' however, retains its attractive appearance, even very ripe, maintaining its desirable characteristics during shipment of the fruit to market.

The fruit of 'Ruby June' and the comparison cultivars were rated based upon commercial appearance using a scale wherein a numerical score of "5" represents the best appearance score. 'Ruby June' rated good, with a score of 3.75, as compared to: 'Sweet Ann' and 'Albion,' each of which have a commercial appearance rating of 4.0; and, 'Aromas' which has a rating of 3.3.

Table. 6 shows the performance of 'Ruby June' compared to 'Sweet Ann,' and the proprietary unpatented varieties designated '42J4' and '17J34.'

TABLE 6

Comparison of Performance of 'Ruby June' to 'Sweet Ann' '42J4' and '17J34'

| Cultivar | Yield grams/plant | Size grams/berry | Appearance Rating 5 = Best |
|---|---|---|---|
| 'Ruby June' | 919 | 30.48 | 3.75 |
| 'Sweet Ann' | 1,738 | 47.5 | 4.0 |

TABLE 6-continued

Comparison of Performance of 'Ruby June' to 'Sweet Ann' '42J4' and '17J34'

| Cultivar | Yield grams/plant | Size grams/berry | Appearance Rating 5 = Best |
|---|---|---|---|
| '42J4' | 1,057 | 33.25 | 4.5 |
| '17J34' | 1,483 | 39.92 | 3.75 |

I claim:

1. A new and distinct strawberry plant named 'Ruby June' as herein described and illustrated by the characterizations set forth above.

* * * * *